United States Patent

Rise et al.

[11] Patent Number: 5,143,067
[45] Date of Patent: Sep. 1, 1992

[54] TOOL FOR IMPLANTABLE NEURAL ELECTRODE

[75] Inventors: Mark Rise, Monticello; Robert J. Klepinski, St. Louis Park, both of Minn.

[73] Assignee: Medtronic, Inc., Minneapolis, Minn.

[21] Appl. No.: 536,524

[22] Filed: Jun. 7, 1990

[51] Int. Cl.⁵ .......................... A61B 5/04; A61N 1/05
[52] U.S. Cl. ................... 128/642; 128/784; 128/785
[58] Field of Search .......... 128/784, 785, 802, 419 C, 128/642

[56] References Cited

U.S. PATENT DOCUMENTS

| | | |
|---|---|---|
| 3,405,715 | 10/1968 | Hagfors . |
| 3,738,368 | 6/1973 | Avery et al. . |
| 3,774,618 | 11/1973 | Avery . |
| 3,822,708 | 7/1974 | Zilber . |
| 3,842,441 | 10/1974 | Kaiser . |
| 3,955,560 | 5/1976 | Stein et al. . |
| 4,573,481 | 3/1986 | Bullara . |
| 4,590,946 | 5/1986 | Loeb . |
| 4,800,882 | 1/1989 | Gianturco . |
| 4,920,979 | 5/1990 | Bullara .............................. 128/784 |

FOREIGN PATENT DOCUMENTS 3709734 10/1988 Fed. Rep. of Germany ...... 128/784

Primary Examiner—Lee S. Cohen
Attorney, Agent, or Firm—Harold R. Patton; Terry L. Wiles; John L. Rooney

[57] ABSTRACT

An implantable electrode system for establishing electrical contact with nerve tissue. The outer substrate of the electrode is a semi-rigid, body compatible, insulating material such as a chronically implantable polymer. The outer substrate is molded as a single structure having a central spine along the longitudinal axis of the electrode. A plurality of fingers extend orthogonally from the central spine, and are bent circularly about a radius of curvature approximating that of the nerve to be contacted. The fingers of the electrode are spread by the retractable channel of the insertion tool during the implant procedure. The retractable channel is placed over the selected nerve and a retraction knob on the handle of the insertion tool is moved in a proximal direction causing the electrode to be ejected on to the nerve. The handle of the insertion tool is curved to require a minimum of exposure of the nerve tissue.

4 Claims, 7 Drawing Sheets

TOOL FOR IMPLANTABLE NEURAL ELECTRODE

CROSS REFERENCE OF CO-PENDING APPLICATIONS

This application is related to Ser. No. 07/446,865, filed Dec. 6, 1989, now U.S. Pat. No. 5,031,621, entitled "Nerve Electrode with Biological Substrate"; Ser. 07/483,455, filed Feb. 22, 1990, now U.S. Pat. No. 5,082,332, entitled "Steroid Eluting Cuff Electrode for Peripheral Nerve Stimulation"; and Ser. No. 07/536,286, now U.S. Pat. No. 5,095,905, filed Jun. 7, 1990, entitled "Implantable Neural Electrode", all of which are assigned to the assignee of this application.

BACKGROUND OF THE INVENTION

1. Field of the Invention

The present invention generally relates to implantable medical devices, and more particularly, relates to implanting electrodes for electrically coupling to nerve tissue.

2. Description of the Prior Art

The use of electrodes to monitor electrical activity and stimulate body tissue is quite old. U.S. Pat. No. 1,662,446 issued to R. H. Wappler teaches an early electrode system. The Wappler electrode is used for acute stimulation only, and is not implantable.

An early stimulation electrode which is chronically implantable is taught by S. I. Schwartz, et al. in U.S. Pat. No. 3,421,511, herein incorporated by reference. U.S. Pat. No. 3,654,933 issued to Hagfors, herein incorporated by reference, teaches an improved stimulation electrode for chronic implantation. Clinical experience with the electrodes taught by Schwartz et al. and Hagfors has shown a potential for excess irritation in certain applications. This irritation results in swelling of the nerve tissue which is exacerbated by the fixed diameter of the cuff of each device after being sutured into place.

U.S. Pat. No. 3,738,368 issued to Avery, et al., U.S. Pat. No. 3,774,618 issued to Avery, and U.S. Pat. No. 3,955,560 issued to Stein, et al. all teach electrodes having fixed diameters after chronic implantation. These electrodes also tend to cover relatively large areas of the nerve tissue, thus depriving nutrient access to great numbers of adjacent nerve cells.

U.S. Pat. No. 4,573,481 issued to Bullara suggests a neural electrode array having a serpentine shape. This shape provides significant access to nutrients by the nerve. This structure, however, provides difficulty in implantation. Because an increase in diameter of the electrode system requires a decrease in length, it is anticipated that the Bullara electrode system does not provide a satisfactory solution to the problem of nerve swelling.

SUMMARY OF THE INVENTION

The present invention overcomes the disadvantages of prior art neural electrodes by providing an electrode system which permits ease of chronic implantation. This procedure produces a minimum of nerve tissue irritation. The desired result is provided by an electrode structure molded of a semirigid polymer having a central spine with a plurality of orthogonal curved fingers. The fingers are not attached to one another to permit the diameter to vary. Enhanced nutrient access is provided by the large open surface area. The implant procedure is easily accomplished by spreading the fingers with a tool and sliding the outer substrate over the nerve tissue.

The inner surface of the fingers is provided with a conducting foil. This foil is coupled proximal to the electrode by conductors positioned along the central spine.

The implantation procedure is accomplished using an implantation tool having a proximal handle and a movable distal channel. The distal channel has a radius of curvature significantly greater than the radius of curvature of the nerve tissue. Mounting the electrode structure on the outer surface of the distal channel causes spreading of the fingers to permit the combination to be easily slipped over the nerve. Curvature of the distal channel enables implantation with a minimum of exposure of the nerve tissue.

The combination is placed over the nerve tissue. A sliding knob located in the proximal handle and coupled to the distal channel is pulled proximally while the electrode structure is held by the electrode stop causing it to be slid from the distal end of the distal channel. The memory of the semi-rigid fingers tends to keep the electrode system in place along the selected nerve.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

Figure 6:
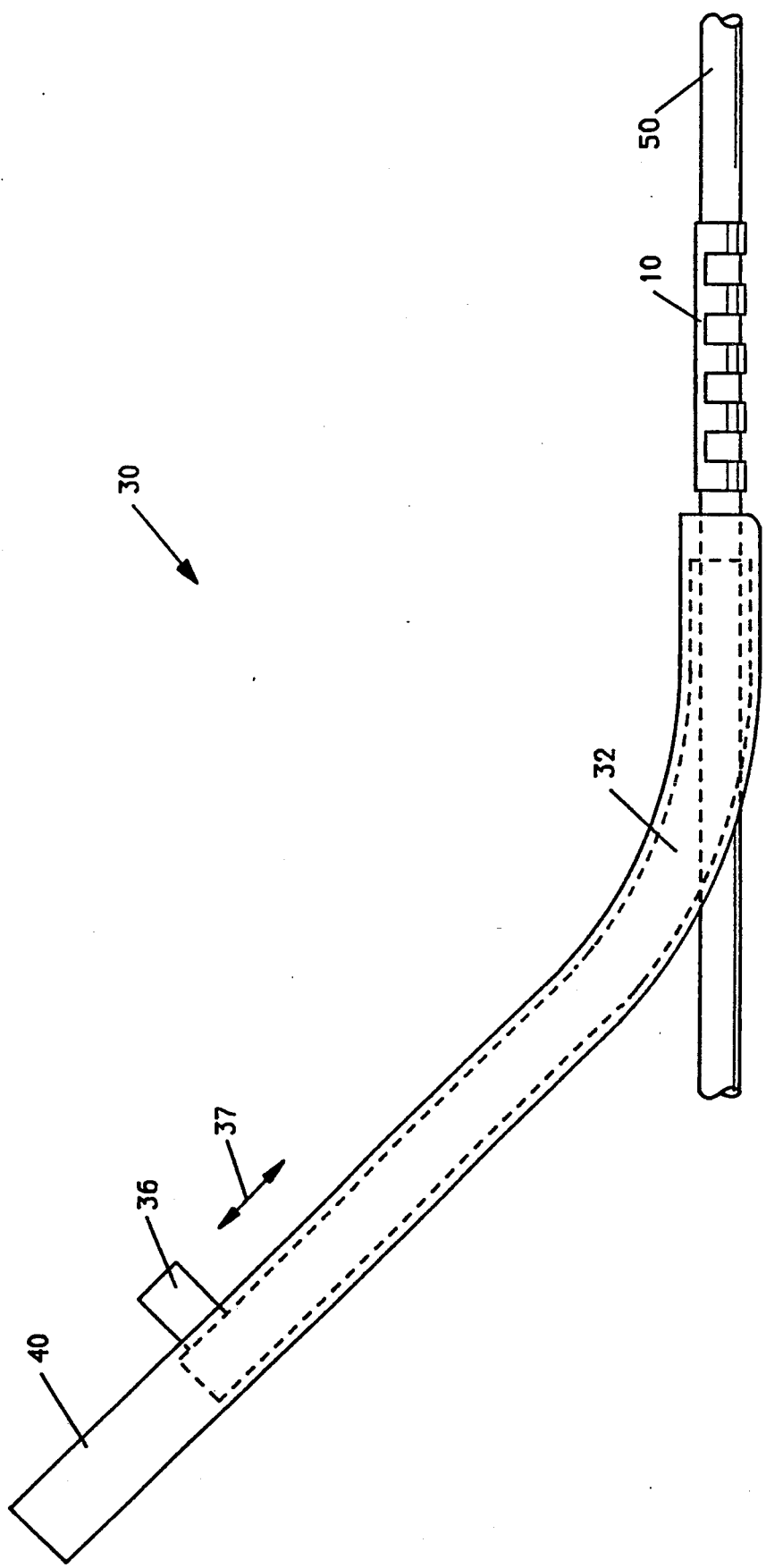

FIG. $ is a top perspective view of the implantation tool; and,

FIG. 6 is a side view of the implantation of the electrode system using the implantation tool.

DETAILED DESCRIPTION OF THE PREFERRED EMBODIMENT

Figure 1:
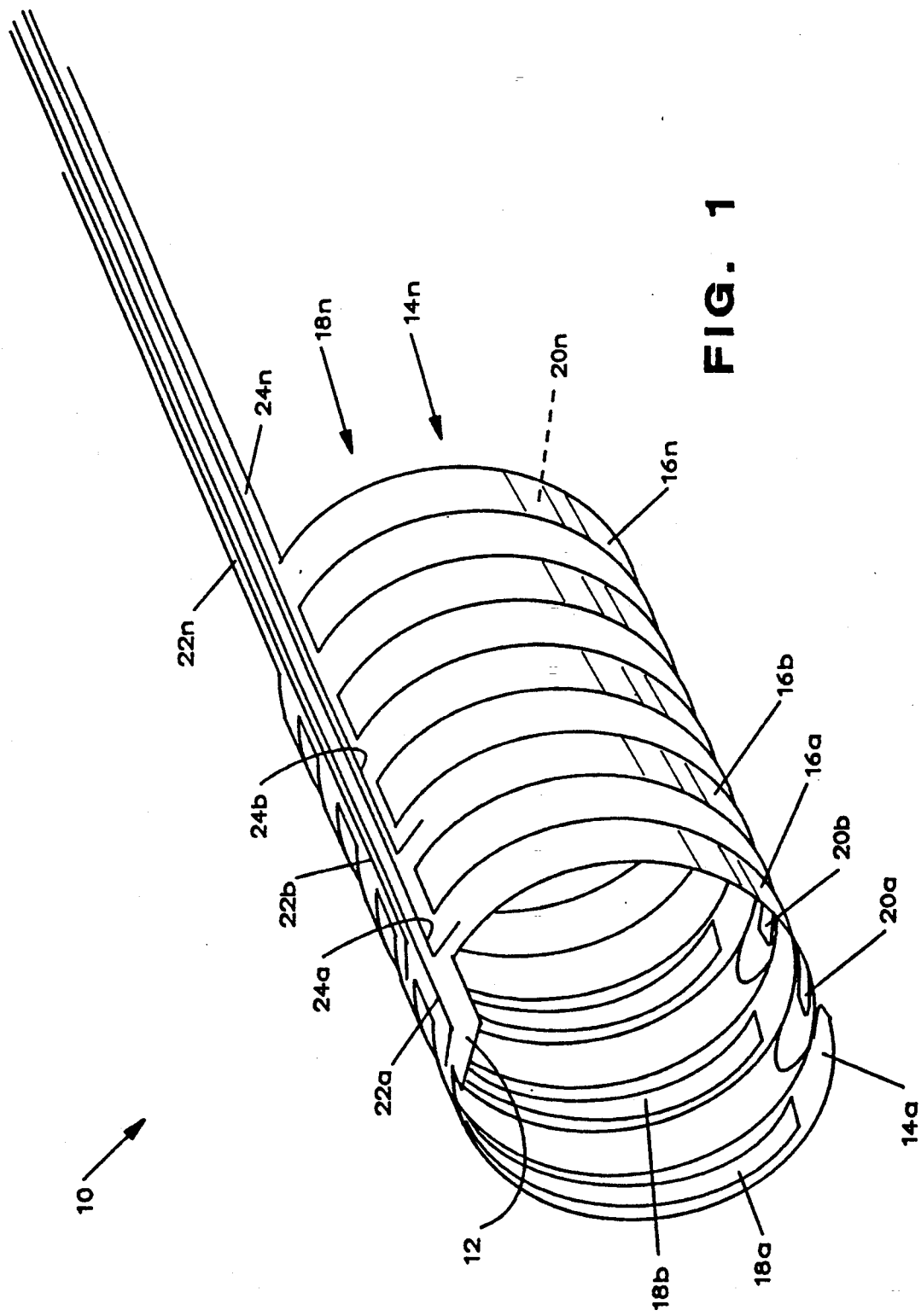
FIG. 1 is a perspective view of the structure of a neural electrode using in the present invention.

FIG. 1 is a perspective view of a neural conductor or electrode used in the present invention. The outer substrate or insulating structure is molded of a semirigid biocompatible polymer material. It has a longitudinal element or central spine 12 which is along the longitudinal axis of the electrode. Fingers 14a–14n extend from central spine 12, and curve in a first direction as shown. Similarly, circumferential elements or fingers 16a–16n extend and bend in the opposite direction. Central spine 12, along with fingers 14a–14n and fingers 16a–16n, are molded as a single piece.

The radius of curvature of fingers 14a–14n and fingers 16a–16n are established to snugly, but not too tightly, fit around the nerve to receive the implant. Because the fingers are molded of a semi-rigid polymer, they can be spread to permit implantation over the nerve and return to the original shape for chronic use.

The fingers are staggered and not connected at the ends as is described in further detail below.

Electrical contact is established using a strip of conducting material placed inside one or more fingers. In this embodiment, electrode element or metallic foil 18a is used on the inner surface of finger 14a, for example. Metallic foil 18a is electrically coupled to the proximal end of electrode 10 (and hence an electronic circuit not shown) using conductor 22a. In the preferred mode electrode lead-in or conductor 22a is vacuum deposited on the inner surface of central spine 12 as shown in the phantom view.

Also in the preferred embodiment, fingers 14b-14n contain metallic foils 1Bb-18n coupled to conductors 22b-22n. Similarly, metallic foils 20a-20n are positioned on the inner surfaces of fingers 16a-16n and coupled to conductors 24a-24n, respectively. Having electrically isolated metallic foils permits the pulse generator electronic circuitry to provide stimulation according to a large number of varying patterns. Alternatively, one or more of the metallic foils may be electrically common to one another rather than electrically isolated.

Figure 2:
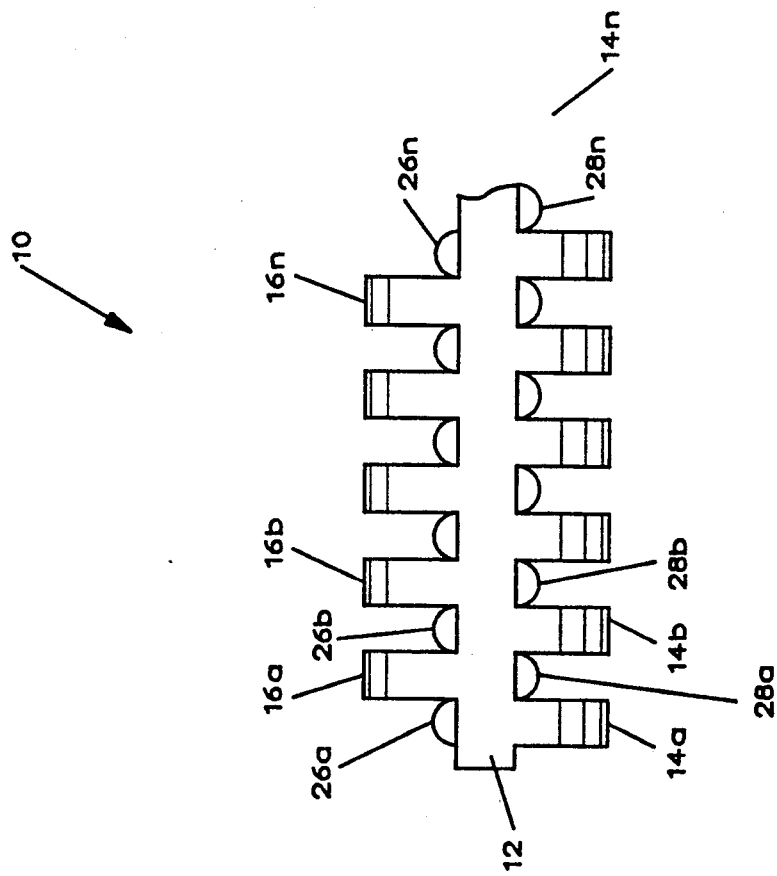
FIG. 2 is a top view of the preferred mode of the neural electrode.

FIG. 2 is a top view of the outer substrate of electrode 10. Fingers 14a-14n are attached orthogonal to central spine 12, and curve under as shown. The length of fingers 14a-14n is chosen to extend about one-half way around the nerve to receive the implant. As can be seen distal tips 26a-26n represent the free ends of fingers 14a-14n, respectively.

Fingers 16a-16n are of equivalent length to fingers 14a-14n, and extend from central spine 12 in the opposite direction as shown. In the preferred embodiment, fingers 14a-14n are staggered from fingers 16a-16n as shown. Fingers 16a-16n terminate in distal tips 28a-28n, respectively. The spacing between fingers may be varied to accommodate the different applications.

Figure 3:
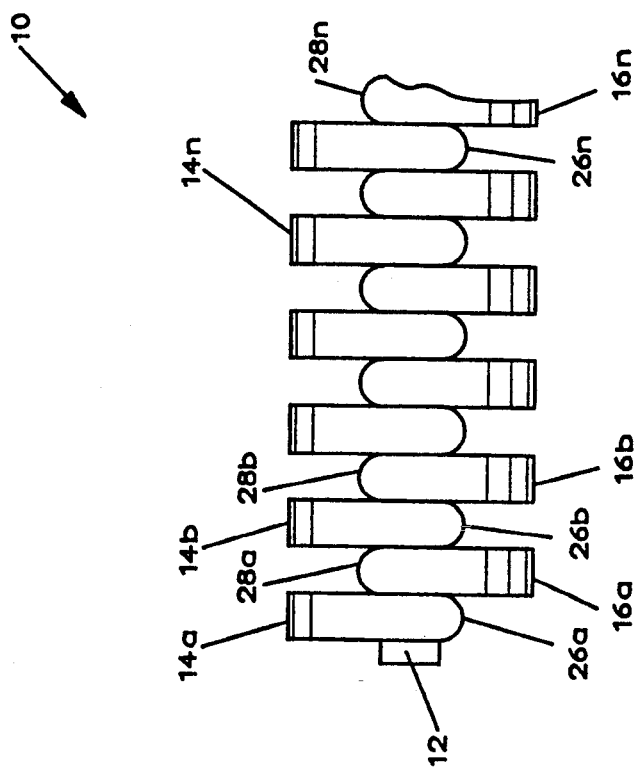
FIG. 3 is a bottom view of a preferred embodiment of the neural electrode.

FIG. 3 is a bottom view of the preferred embodiment. All components are as previously described.

Figure 3A:
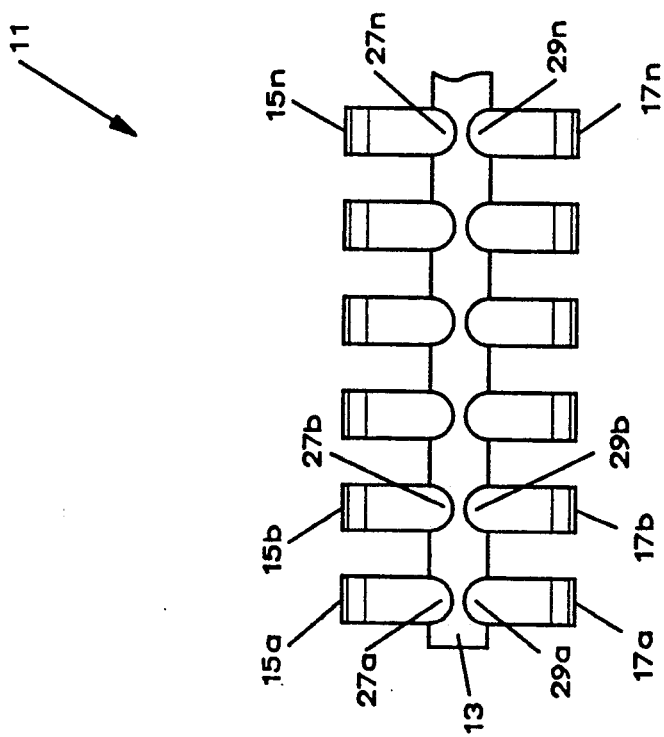
FIG. 3A is a bottom view of an alternate embodiment of the neural electrode.

FIG. 3A is a bottom view of an alternative embodiment of electrode 11. In this mode fingers 15a-15n are not staggered from fingers 17a-17n in attachment to central spine 13. This differs from the preferred mode in that spreading of the fingers results in no overlap at all, and therefore greater nerve surface area for nutrient access.

Figure 4:
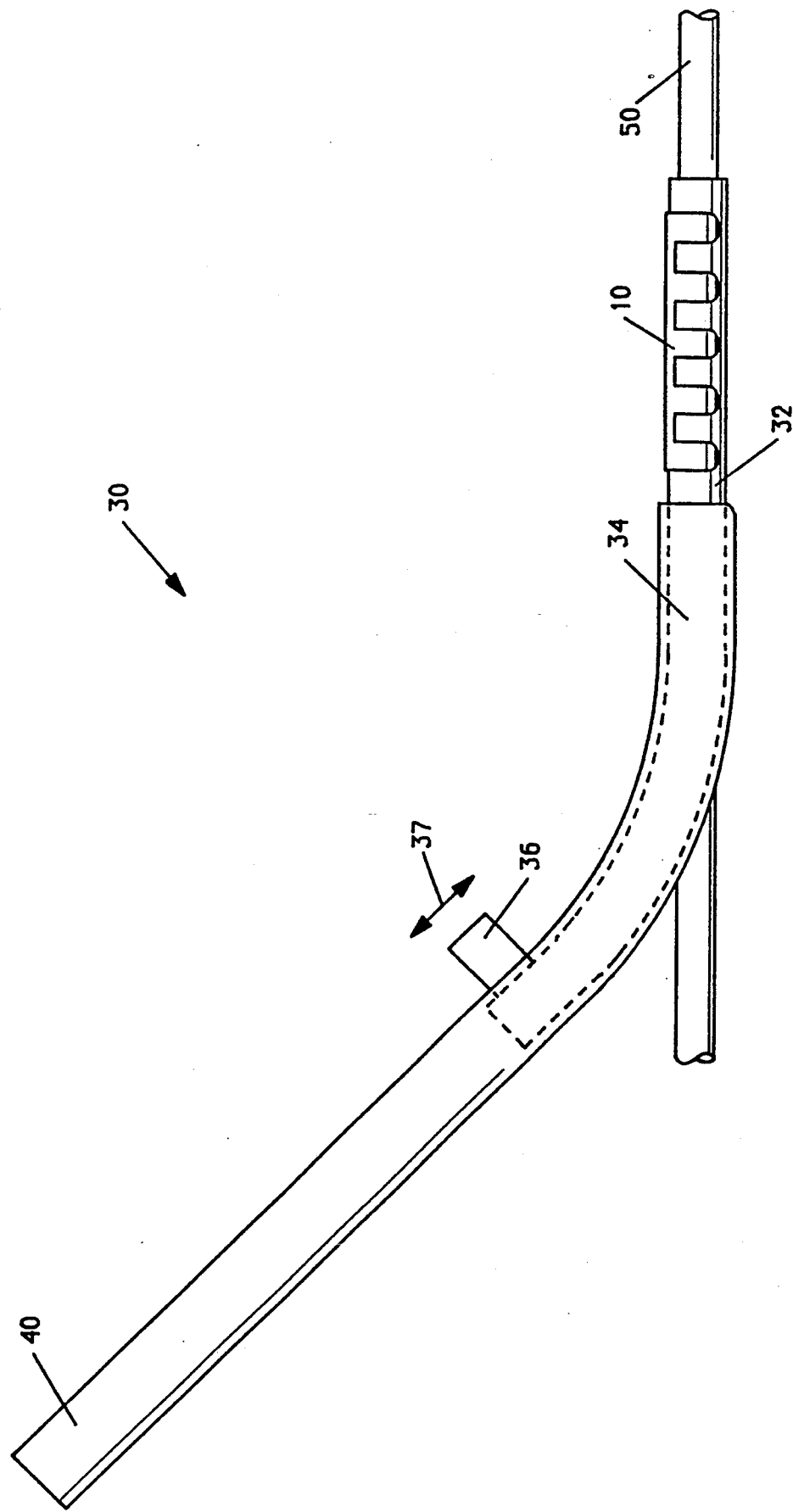
FIG. 4 is a side view of the neural electrode mounted on the implantation tool.

FIG. 4 is a side view of implantation tool 30. It has a handle 40 (only partially shown) which is held by the implanting physician. Handle 40 is hollow to accommodate flexible distal channel 32, which is a channel opening downward. The lateral radius of curvature of distal channel 3 must be greater than the diameter of the nerve to receive the implant. Similarly, the opening at the bottom of distal channel 32 must be wider than the diameter of the nerve to receive the implant (see also Fib. 5). The portion of distal channel 32 which is distal to handle 40 must be at least as long as electrode 10 such that electrode 10, with its fingers spread, fits completely over distal channel 32.

During implantation, it is desirable to expose only the minimum amount of nerve surface. To assist in implantation, distal channel 32 curves at bend 34. This permits distal channel 32 to be withdrawn away from the implant site.

Retracting knob 36 is attached to the proximal end of distal channel 32 as is shown in phantom. Because of slot 35 in handle 40 (see also FIG. 5), retracting knob 36 is free to move in the direction of arrow 37. Retracting knob 36 is shown in its most distal position.

Figure 5:
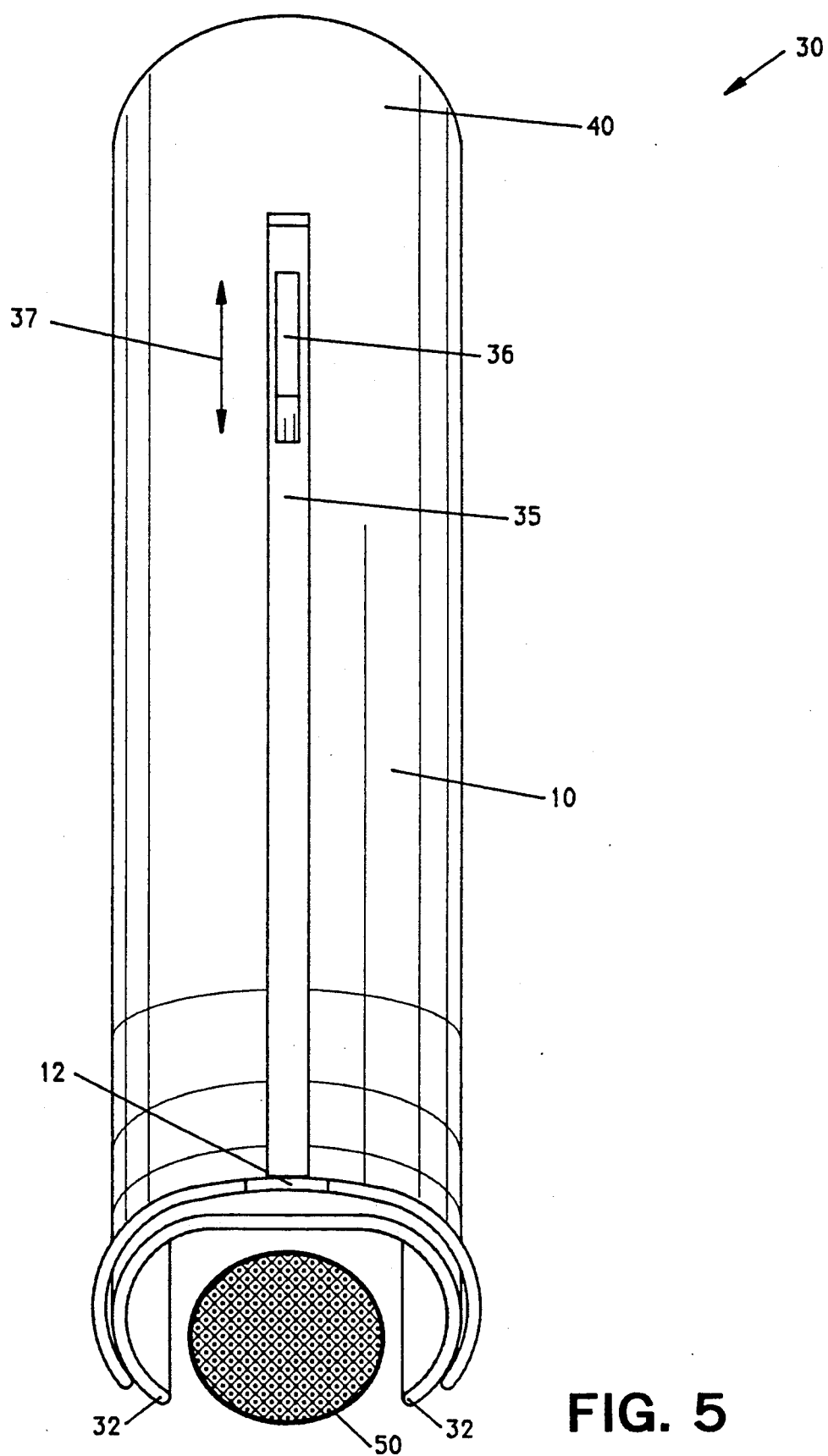

FIG. 5 is an perspective end view of implantation tool 30 disposed over nerve 50. Note that distal channel 32 conveniently slides over nerve 50. Electrode 10 has its fingers spread to enable it to be positioned on the outer surface of distal channel 32.

FIG. 6 shows electrode 10 as partially implanted aruond nerve 50 using implantation tool 30. The implantation is completed as distal channel 32 is slowly (shown in phantom) retracted into handle 40 by proximal motion of retracting knob 36 and electrode 10 is held in a fixed position with respect to nerve 50. As fingers 14a-14n (and fingers 16a-16n, not shown) are slid from the distal end of distal channel 32, they tend to resume their original cylindrical shape about nerve 50. The diameter of the resulting cylinder may be chosen at manufacture to fit loosely or snugly about nerve 50 as medical requirements might dictate.

Having thus described the preferred embodiments of the present invention, those of skill in the art will be able to apply the teachings found herein to other embodiments without deviating from the scope of the claims hereto attached.

I CLAIM:

1. An electrode system for implanting on nerve tissue having an outside diameter comprising:
   a. an implantable electrode having a generally cylindrical body with a plurality of flexible circumferentially directed elements and having an electrically conductive surface;
   b. a channel having an interior size greater than said outside diameter of said nerve tissue whereby said plurality of flexible circumferentially directed elements may be spread to position said implantable electrode on said channel and having said implantable electrode positioned thereon; and
   c. means coupled to said channel for ejecting said implantable electrode from said channel.

2. An electrode system according to claim 1 further comprising a handle attached to said channel and said ejecting means.

3. An electrode system according to claim 2 wherein said channel is retractably inserted within said handle.

4. An electrode system according to claim 3 wherein said ejecting means is slidably mounted on said handle.

* * * * *